United States Patent
Liebowitz

(10) Patent No.: US 11,998,213 B2
(45) Date of Patent: Jun. 4, 2024

(54) IMPLANT DELIVERY WITH MODIFIED DETACHMENT FEATURE AND PULL WIRE ENGAGEMENT

(71) Applicant: DePuy Synthes Products, Inc., Raynham, MA (US)

(72) Inventor: Joshua Liebowitz, Raynham, MA (US)

(73) Assignee: DEPUY SYNTHES PRODUCTS, INC., Raynham, MA (US)

( * ) Notice: Subject to any disclaimer, the term of this patent is extended or adjusted under 35 U.S.C. 154(b) by 393 days.

(21) Appl. No.: 17/375,375

(22) Filed: Jul. 14, 2021

(65) Prior Publication Data

US 2023/0019940 A1 Jan. 19, 2023

(51) Int. Cl.
*A61B 17/12* (2006.01)
*A61M 25/01* (2006.01)

(52) U.S. Cl.
CPC ... *A61B 17/12154* (2013.01); *A61M 25/0147* (2013.01); *A61B 2017/12054* (2013.01)

(58) Field of Classification Search
CPC .......... A61B 17/12154; A61B 17/1214; A61B 2017/12054; A61B 2017/1205; A61B 2017/12077; A61M 25/0147
See application file for complete search history.

(56) References Cited

U.S. PATENT DOCUMENTS

| | | | |
|---|---|---|---|
| 3,429,408 A | 2/1969 | Maker et al. | |
| 5,108,407 A | 4/1992 | Geremia et al. | |
| 5,122,136 A | 6/1992 | Guglielmi et al. | |
| 5,250,071 A | 10/1993 | Palermo | |
| 5,263,964 A | 11/1993 | Purdy | |
| 5,334,210 A | 8/1994 | Gianturco | |
| 5,350,397 A | 9/1994 | Palermo et al. | |
| 5,382,259 A | 1/1995 | Phelps et al. | |
| 5,484,409 A | 1/1996 | Atkinson et al. | |

(Continued)

FOREIGN PATENT DOCUMENTS

| | | | |
|---|---|---|---|
| EP | 1728478 A1 | 12/2006 | |
| EP | 1985244 A2 | 10/2008 | |

(Continued)

OTHER PUBLICATIONS

Extended European Search Report for European Application No. 20196478.0, dated Jan. 25, 2021, 11 Pages.

(Continued)

*Primary Examiner* — Kathleen S Holwerda
(74) *Attorney, Agent, or Firm* — TROUTMAN PEPPER HAMILTON SANDERS LLP

(57) ABSTRACT

An embolic implant includes a detachment feature configured to engage and be released from a delivery member's engagement system. The engagement system can include a loop wire extending through an opening of the detachment feature a pull wire extending through the loop wire to secure the detachment feature to a delivery tube of the delivery member. The detachment feature can include a distal extension configured to engage a distal end of the pull wire to inhibit the pull wire from moving distally into the implant. The detachment feature can also include a sleeve to align the pull wire to the distal extension and/or provide a friction force against the pull wire to inhibit longitudinal movement of the distal end of the pull wire.

16 Claims, 10 Drawing Sheets

(56) References Cited

U.S. PATENT DOCUMENTS

| | | |
|---|---|---|
| 5,569,221 A | 10/1996 | Houser et al. |
| 5,853,418 A * | 12/1998 | Ken ................. A61B 17/12113 606/198 |
| 5,899,935 A | 5/1999 | Ding |
| 5,925,059 A | 7/1999 | Palermo et al. |
| 6,113,622 A | 9/2000 | Hieshima |
| 6,203,547 B1 | 3/2001 | Nguyen et al. |
| 6,391,037 B1 | 5/2002 | Greenhalgh |
| 6,454,780 B1 | 9/2002 | Wallace |
| 6,506,204 B2 | 1/2003 | Mazzocchi |
| 6,561,988 B1 | 5/2003 | Turturro et al. |
| 7,367,987 B2 | 5/2008 | Balgobin et al. |
| 7,371,251 B2 | 5/2008 | Mitelberg et al. |
| 7,371,252 B2 | 5/2008 | Balgobin et al. |
| 7,377,932 B2 | 5/2008 | Mitelberg et al. |
| 7,708,754 B2 | 5/2010 | Balgobin et al. |
| 7,708,755 B2 | 5/2010 | Davis, III et al. |
| 7,799,052 B2 | 9/2010 | Balgobin et al. |
| 7,811,305 B2 | 10/2010 | Balgobin et al. |
| 7,819,891 B2 | 10/2010 | Balgobin et al. |
| 7,819,892 B2 | 10/2010 | Balgobin et al. |
| 7,901,444 B2 | 3/2011 | Slazas |
| 7,942,894 B2 | 5/2011 | West |
| 7,985,238 B2 | 7/2011 | Balgobin et al. |
| 8,062,325 B2 | 11/2011 | Mitelberg et al. |
| 8,333,796 B2 | 12/2012 | Tompkins et al. |
| 8,449,591 B2 | 5/2013 | Litzenberg et al. |
| 8,974,488 B2 | 3/2015 | Tan et al. |
| 9,155,540 B2 | 10/2015 | Lorenzo |
| 9,232,992 B2 | 1/2016 | Heidner |
| 9,314,326 B2 | 4/2016 | Wallace et al. |
| 9,532,792 B2 | 1/2017 | Galdonik et al. |
| 9,532,873 B2 | 1/2017 | Kelley |
| 9,533,344 B2 | 1/2017 | Monetti et al. |
| 9,539,011 B2 | 1/2017 | Chen et al. |
| 9,539,022 B2 | 1/2017 | Bowman |
| 9,539,122 B2 | 1/2017 | Burke et al. |
| 9,539,382 B2 | 1/2017 | Nelson |
| 9,549,830 B2 | 1/2017 | Bruszewski et al. |
| 9,554,805 B2 | 1/2017 | Tompkins et al. |
| 9,561,125 B2 | 2/2017 | Bowman et al. |
| 9,572,982 B2 | 2/2017 | Burnes et al. |
| 9,579,484 B2 | 2/2017 | Barnell |
| 9,585,642 B2 | 3/2017 | Dinsmoor et al. |
| 9,615,832 B2 | 4/2017 | Bose et al. |
| 9,615,951 B2 | 4/2017 | Bennett et al. |
| 9,622,753 B2 | 4/2017 | Cox |
| 9,636,115 B2 | 5/2017 | Henry et al. |
| 9,636,439 B2 | 5/2017 | Chu et al. |
| 9,642,675 B2 | 5/2017 | Werneth et al. |
| 9,655,633 B2 | 5/2017 | Leynov et al. |
| 9,655,645 B2 | 5/2017 | Staunton |
| 9,655,989 B2 | 5/2017 | Cruise et al. |
| 9,662,120 B2 | 5/2017 | Lagodzki et al. |
| 9,662,129 B2 | 5/2017 | Galdonik et al. |
| 9,662,238 B2 | 5/2017 | Dwork et al. |
| 9,662,425 B2 | 5/2017 | Lilja et al. |
| 9,668,898 B2 | 6/2017 | Wong |
| 9,675,477 B2 | 6/2017 | Thompson |
| 9,675,782 B2 | 6/2017 | Connolly |
| 9,676,022 B2 | 6/2017 | Ensign et al. |
| 9,692,557 B2 | 6/2017 | Murphy |
| 9,693,852 B2 | 7/2017 | Lam et al. |
| 9,700,262 B2 | 7/2017 | Janik et al. |
| 9,700,399 B2 | 7/2017 | Acosta-Acevedo |
| 9,717,421 B2 | 8/2017 | Griswold et al. |
| 9,717,500 B2 | 8/2017 | Tieu et al. |
| 9,717,502 B2 | 8/2017 | Teoh et al. |
| 9,724,103 B2 | 8/2017 | Cruise et al. |
| 9,724,526 B2 | 8/2017 | Strother et al. |
| 9,750,565 B2 | 9/2017 | Bloom et al. |
| 9,757,260 B2 | 9/2017 | Greenan |
| 9,764,111 B2 | 9/2017 | Gulachenski |
| 9,770,251 B2 | 9/2017 | Bowman et al. |
| 9,770,577 B2 | 9/2017 | Li et al. |
| 9,775,621 B2 | 10/2017 | Tompkins et al. |
| 9,775,706 B2 | 10/2017 | Paterson et al. |
| 9,775,732 B2 | 10/2017 | Khenansho |
| 9,788,800 B2 | 10/2017 | Mayoras, Jr. |
| 9,795,391 B2 | 10/2017 | Saatchi et al. |
| 9,801,980 B2 | 10/2017 | Karino et al. |
| 9,808,599 B2 | 11/2017 | Bowman et al. |
| 9,833,252 B2 | 12/2017 | Sepetka et al. |
| 9,833,604 B2 | 12/2017 | Lam et al. |
| 9,833,625 B2 | 12/2017 | Waldhauser et al. |
| 9,918,718 B2 | 3/2018 | Lorenzo |
| 10,034,670 B2 | 7/2018 | Elgård et al. |
| 10,282,851 B2 | 5/2019 | Gorochow |
| 10,285,710 B2 | 5/2019 | Lorenzo et al. |
| 10,517,604 B2 | 12/2019 | Bowman et al. |
| 10,806,402 B2 | 10/2020 | Cadieu et al. |
| 10,806,461 B2 | 10/2020 | Lorenzo |
| 10,806,462 B2 | 10/2020 | Lorenzo |
| 10,888,331 B2 | 1/2021 | Pederson et al. |
| 11,051,928 B2 | 7/2021 | Casey et al. |
| 2001/0049519 A1 | 12/2001 | Holman et al. |
| 2002/0072705 A1 | 6/2002 | Vrba et al. |
| 2002/0165569 A1 | 11/2002 | Ramzipoor et al. |
| 2004/0002731 A1 | 1/2004 | Aganon et al. |
| 2004/0034363 A1 | 2/2004 | Wilson et al. |
| 2004/0059367 A1 | 3/2004 | Davis et al. |
| 2004/0087964 A1 | 5/2004 | Diaz et al. |
| 2005/0149108 A1* | 7/2005 | Cox ................. A61B 17/12022 606/200 |
| 2006/0025802 A1 | 2/2006 | Sowers |
| 2006/0064151 A1 | 3/2006 | Guterman |
| 2006/0116711 A1 | 6/2006 | Elliott et al. |
| 2006/0135021 A1 | 6/2006 | Calhoun et al. |
| 2006/0276824 A1 | 12/2006 | Mitelberg et al. |
| 2006/0276825 A1 | 12/2006 | Mitelberg et al. |
| 2006/0276826 A1 | 12/2006 | Mitelberg et al. |
| 2006/0276827 A1 | 12/2006 | Mitelberg et al. |
| 2006/0276830 A1 | 12/2006 | Balgobin et al. |
| 2006/0276833 A1 | 12/2006 | Balgobin et al. |
| 2007/0010850 A1 | 1/2007 | Balgobin et al. |
| 2007/0083132 A1 | 4/2007 | Sharrow |
| 2007/0233168 A1 | 10/2007 | Davis et al. |
| 2007/0270903 A1 | 11/2007 | Davis, III et al. |
| 2008/0027561 A1 | 1/2008 | Mitelberg et al. |
| 2008/0035160 A1 | 2/2008 | Woodson et al. |
| 2008/0045997 A1 | 2/2008 | Balgobin et al. |
| 2008/0082113 A1 | 4/2008 | Bishop et al. |
| 2008/0097462 A1 | 4/2008 | Mitelberg et al. |
| 2008/0119887 A1 | 5/2008 | Que et al. |
| 2008/0281350 A1 | 11/2008 | Sepetka |
| 2008/0300616 A1* | 12/2008 | Que ................. A61B 17/12113 606/191 |
| 2008/0306503 A1 | 12/2008 | Que et al. |
| 2009/0062726 A1 | 3/2009 | Ford et al. |
| 2009/0099592 A1* | 4/2009 | Buiser ................. A61B 17/1214 606/53 |
| 2009/0312748 A1 | 12/2009 | Johnson et al. |
| 2010/0114017 A1 | 5/2010 | Lenker et al. |
| 2010/0160944 A1 | 6/2010 | Teoh et al. |
| 2010/0324649 A1 | 12/2010 | Mattsson |
| 2011/0092997 A1* | 4/2011 | Kang ................. A61B 17/12154 606/191 |
| 2011/0295303 A1 | 12/2011 | Freudenthal |
| 2012/0035707 A1 | 2/2012 | Mitelberg et al. |
| 2012/0041472 A1 | 2/2012 | Tan et al. |
| 2012/0283768 A1 | 11/2012 | Cox et al. |
| 2013/0066413 A1 | 3/2013 | Jin et al. |
| 2013/0338701 A1 | 12/2013 | Wilson et al. |
| 2014/0058435 A1 | 2/2014 | Jones et al. |
| 2014/0135812 A1 | 5/2014 | Divino et al. |
| 2014/0200607 A1 | 7/2014 | Sepetka et al. |
| 2014/0207175 A1 | 7/2014 | Aggerholm |
| 2014/0277085 A1 | 9/2014 | Mirigian et al. |
| 2014/0277092 A1 | 9/2014 | Teoh et al. |
| 2014/0277093 A1 | 9/2014 | Guo et al. |
| 2015/0182227 A1 | 7/2015 | Le et al. |
| 2015/0230802 A1 | 8/2015 | Lagodzki et al. |
| 2015/0335333 A1 | 11/2015 | Jones et al. |
| 2016/0022275 A1 | 1/2016 | Garza |

(56) References Cited

U.S. PATENT DOCUMENTS

| | | |
|---|---|---|
| 2016/0157869 A1 | 6/2016 | Elgård et al. |
| 2016/0228125 A1 | 8/2016 | Pederson, Jr. et al. |
| 2016/0310304 A1 | 10/2016 | Mialhe |
| 2016/0346508 A1 | 12/2016 | Williams et al. |
| 2017/0007264 A1 | 1/2017 | Cruise et al. |
| 2017/0007265 A1 | 1/2017 | Guo et al. |
| 2017/0020670 A1 | 1/2017 | Murray et al. |
| 2017/0020700 A1 | 1/2017 | Bienvenu et al. |
| 2017/0027640 A1 | 2/2017 | Kunis et al. |
| 2017/0027692 A1 | 2/2017 | Bonhoeffer et al. |
| 2017/0027725 A1 | 2/2017 | Argentine |
| 2017/0035436 A1 | 2/2017 | Morita |
| 2017/0035567 A1 | 2/2017 | Duffy |
| 2017/0042548 A1 | 2/2017 | Lam |
| 2017/0049596 A1 | 2/2017 | Schabert |
| 2017/0071737 A1 | 3/2017 | Kelley |
| 2017/0072452 A1 | 3/2017 | Monetti et al. |
| 2017/0079671 A1 | 3/2017 | Morero et al. |
| 2017/0079680 A1 | 3/2017 | Bowman |
| 2017/0079766 A1 | 3/2017 | Wang et al. |
| 2017/0079767 A1 | 3/2017 | Leon-Yip |
| 2017/0079812 A1 | 3/2017 | Lam et al. |
| 2017/0079817 A1 | 3/2017 | Sepetka et al. |
| 2017/0079819 A1 | 3/2017 | Pung et al. |
| 2017/0079820 A1 | 3/2017 | Lam et al. |
| 2017/0086851 A1 | 3/2017 | Wallace et al. |
| 2017/0086996 A1 | 3/2017 | Peterson et al. |
| 2017/0095259 A1 | 4/2017 | Tompkins et al. |
| 2017/0100126 A1 | 4/2017 | Bowman et al. |
| 2017/0100141 A1 | 4/2017 | Morero et al. |
| 2017/0100143 A1 | 4/2017 | Granfield |
| 2017/0100183 A1 | 4/2017 | Iaizzo et al. |
| 2017/0105739 A1 | 4/2017 | Dias et al. |
| 2017/0113023 A1 | 4/2017 | Steingisser et al. |
| 2017/0147765 A1 | 5/2017 | Mehta |
| 2017/0151032 A1 | 6/2017 | Loisel |
| 2017/0165062 A1 | 6/2017 | Rothstein |
| 2017/0165065 A1 | 6/2017 | Rothstein et al. |
| 2017/0165454 A1 | 6/2017 | Tuohy et al. |
| 2017/0172581 A1 | 6/2017 | Bose et al. |
| 2017/0172766 A1 | 6/2017 | Vong et al. |
| 2017/0172772 A1 | 6/2017 | Khenansho |
| 2017/0189033 A1 | 7/2017 | Sepetka et al. |
| 2017/0189035 A1 | 7/2017 | Porter |
| 2017/0215902 A1 | 8/2017 | Leynov et al. |
| 2017/0216484 A1 | 8/2017 | Cruise et al. |
| 2017/0224350 A1 | 8/2017 | Shimizu et al. |
| 2017/0224355 A1 | 8/2017 | Bowman et al. |
| 2017/0224467 A1 | 8/2017 | Piccagli et al. |
| 2017/0224511 A1 | 8/2017 | Dwork et al. |
| 2017/0224953 A1 | 8/2017 | Tran et al. |
| 2017/0231749 A1 | 8/2017 | Perkins et al. |
| 2017/0245864 A1 | 8/2017 | Franano et al. |
| 2017/0245885 A1 | 8/2017 | Lenker |
| 2017/0252064 A1 | 9/2017 | Staunton |
| 2017/0258476 A1 | 9/2017 | Hayakawa et al. |
| 2017/0265983 A1 | 9/2017 | Lam et al. |
| 2017/0281192 A1 | 10/2017 | Tieu et al. |
| 2017/0281331 A1 | 10/2017 | Perkins et al. |
| 2017/0281344 A1 | 10/2017 | Costello |
| 2017/0281909 A1 | 10/2017 | Northrop et al. |
| 2017/0281912 A1 | 10/2017 | Melder et al. |
| 2017/0290593 A1 | 10/2017 | Cruise et al. |
| 2017/0290654 A1 | 10/2017 | Sethna |
| 2017/0296324 A1 | 10/2017 | Argentine |
| 2017/0296325 A1 | 10/2017 | Marrocco et al. |
| 2017/0303939 A1 | 10/2017 | Greenhalgh et al. |
| 2017/0303942 A1 | 10/2017 | Greenhalgh et al. |
| 2017/0303947 A1 | 10/2017 | Greenhalgh et al. |
| 2017/0303948 A1 | 10/2017 | Wallace et al. |
| 2017/0304041 A1 | 10/2017 | Argentine |
| 2017/0304097 A1 | 10/2017 | Corwin et al. |
| 2017/0304595 A1 | 10/2017 | Nagasrinivasa et al. |
| 2017/0312109 A1 | 11/2017 | Le |
| 2017/0312484 A1 | 11/2017 | Shipley et al. |
| 2017/0316561 A1 | 11/2017 | Helm et al. |
| 2017/0319826 A1 | 11/2017 | Bowman et al. |
| 2017/0333228 A1 | 11/2017 | Orth et al. |
| 2017/0333236 A1 | 11/2017 | Greenan |
| 2017/0333678 A1 | 11/2017 | Bowman et al. |
| 2017/0340383 A1 | 11/2017 | Bloom et al. |
| 2017/0348014 A1 | 12/2017 | Wallace et al. |
| 2017/0348514 A1 | 12/2017 | Guyon et al. |
| 2018/0028779 A1 | 2/2018 | von Oepen et al. |
| 2018/0250150 A1 | 9/2018 | Majercak et al. |
| 2018/0280667 A1 | 10/2018 | Keren |
| 2018/0289375 A1 | 10/2018 | Hebert et al. |
| 2018/0325706 A1 | 11/2018 | Hebert et al. |
| 2019/0192162 A1* | 6/2019 | Lorenzo .......... A61B 17/12022 |
| 2019/0255290 A1 | 8/2019 | Snyder et al. |
| 2019/0328398 A1 | 10/2019 | Lorenzo |
| 2021/0001082 A1 | 1/2021 | Lorenzo et al. |

FOREIGN PATENT DOCUMENTS

| | | |
|---|---|---|
| EP | 3092956 A1 | 11/2016 |
| EP | 3501427 A1 | 6/2019 |
| EP | 3760139 A2 | 1/2021 |
| JP | 2006-334408 A | 12/2006 |
| JP | 2012-523943 A | 10/2012 |
| JP | 2013-78584 A | 5/2013 |
| WO | WO 2012/158152 A1 | 11/2012 |

OTHER PUBLICATIONS

Extended European Search Report for European Application No. 22184571.2, dated Dec. 8, 2022, 8 pages.

Extended European Search Report issued in European Patent Application No. 22 18 4571 dated Dec. 6, 2022.

* cited by examiner

IMPLANT DELIVERY WITH MODIFIED DETACHMENT FEATURE AND PULL WIRE ENGAGEMENT

FIELD OF INVENTION

The present invention generally relates to implantable medical devices, and more particularly, to engagement and detachment features that can secure an implantable medical device to a delivery system during delivery of the implant and can release the implantable medical device from the delivery system.

BACKGROUND

Aneurysms can be intravascularly treated by delivering a treatment device to the aneurysm to fill the sac of the aneurysm with embolic material and/or block the neck of the aneurysm to inhibit blood flow into the aneurysm. When filling the aneurysm sac, the embolic material can promote blood clotting to create a thrombotic mass within the aneurysm. When treating the aneurysm neck without substantially filling the aneurysm sac, blood flow into the neck of the aneurysm can be inhibited to induce venous stasis in the aneurysm and facilitate natural formation of a thrombotic mass within the aneurysm.

In some current treatments, multiple embolic coils, and other embolic implants (e.g. braids) are used to either fill the aneurysm sac or treat the entrance of the aneurysm neck. An embolic implant is attached to a tubular delivery member and delivered via a delivery catheter to an aneurysm. During delivery, the embolic implant can be engaged to the delivery member's implant engagement/deployment system (referred to herein equivalently as an "engagement system" or "deployment system"). When the embolic implant is in position, the deployment system can release the implant, the implant can be left implanted, and the delivery member can be retracted. Some treatments utilize a mechanical engagement/deployment system that can be actuated by a physician to release the implant by pulling one or more wires or other elongated members referred to generically herein as a "pull wire".

Some of the challenges that have been associated with delivering and deploying embolic implants with delivery members having mechanical engagement systems include premature release of the implant during navigation of tortuous anatomy and/or movement of the delivery member. Premature release can be due to push back from densely packed treatment sites.

There is therefore a need for improved methods, devices, and systems to facilitate implantation of embolic coils and other implants facing similar challenges.

SUMMARY

Example systems, implants, and methods associated with the same are presented herein which generally include an embolic implant, such as an embolic coil or a tubular braid, that includes a detachment feature configured to engage and be released from a delivery member's engagement system (deployment system). The delivery member can include an elongated delivery tube and the engagement system can include a pull wire extending through the delivery tube and a loop wire attached near a distal end of the delivery tube. To secure the implant to the delivery tube, the loop wire can be positioned through an opening of the detachment feature and a distal end of the pull wire can be positioned through an opening of the loop wire. The detachment feature can include a distal extension configured to engage a distal end of the pull wire and inhibit the pull wire from moving distally into the implant. The detachment feature can also include a sleeve to align the pull wire to the distal extension and/or provide a friction force against the pull wire to inhibit longitudinal movement of the distal end of the pull wire.

An example system can include an elongated delivery tube, an embolic implant, a loop wire, and a pull wire. The elongated delivery tube can be configured to traverse vasculature. The elongated delivery tube extends along a longitudinal axis of the system. The embolic implant includes a detachment feature. The detachment feature can have a distal extension and a proximal opening. The loop wire can be affixed to the delivery tube. The loop wire can extend through the proximal opening of the detachment feature. The pull wire extends through the delivery tube, extends through an opening in the loop wire, and can be inhibited from moving distally by the distal extension of the detachment feature.

The detachment feature can further include a sleeve into which the pull wire extends. The sleeve can provide a friction force against the pull wire. The sleeve can further include an elastic material positioned on at least a portion of a perimeter of an opening of the sleeve. The elastic material can provide the friction force against the pull wire. The pull wire can extend through the opening of the sleeve. Additionally, or alternative to providing the friction force, the sleeve can be positioned to align the pull wire longitudinally with the distal extension.

The detachment feature can have a distal portion that includes the distal extension and a proximal portion that includes the proximal opening. The proximal portion can have a proximal width that is greater than a distal width of the distal portion.

The embolic implant can include an embolic coil. The distal portion of the detachment feature can be positioned within a lumen of the embolic coil. The distal portion can include the distal extension. The proximal portion of the detachment feature can extend proximally from a proximal end of the embolic coil. The proximal portion can include the proximal opening.

The distal portion of the detachment feature can further include a distal opening. The embolic implant can further include a stretch resistant fiber passing through the distal opening and extending through the lumen of the embolic coil to a distal end of the embolic coil. The stretch resistant fiber can be effective to limit separation of windings of the embolic coil as the embolic coil is under tension.

The detachment feature can have a first shoulder affixed to the proximal end of the embolic coil and a second shoulder affixed to the proximal end of the embolic coil. The first shoulder can be longitudinally offset in relation to the second shoulder.

The embolic implant can include a tubular braid.

The elongated delivery tube can have notches extending proximally from a distal end of the delivery tube. The proximal portion of the detachment feature can be positioned within the notches.

The proximal opening in the detachment feature can have an atraumatic surface against the loop wire.

The detachment feature can have a substantially planar first surface and a second surface opposite the first surface. The distal extension can be disposed on the second surface.

The pull wire can be in compression longitudinally within the delivery tube.

An example implant can include an embolic tube and a detachment feature. The embolic tube can have a lumen therethrough. The embolic tube can define a longitudinal axis of the implant. The detachment feature can include a distal portion extending within the lumen, a proximal portion extending proximally from a proximal end of the embolic tube, a proximal opening configured to receive a loop wire therethrough, and a sleeve comprising a longitudinal opening configured to receive a pull wire.

The detachment feature further can further have a distal extension positioned distally of the sleeve and aligned longitudinally with the opening.

The sleeve can include an elastic material on at least a portion of a perimeter of the opening.

An example method for delivering an implant having a detachment feature can include one or more of the following steps presented in no particular order, and the method can include additional steps not included here. The distal end of the pull wire can be inhibited from moving distally by pressing a distal end of a pull wire into a distal extension of the detachment feature. An implant delivery system can be delivered through vasculature, the implant delivery system including an elongated delivery tube, the implant, and the pull wire. The pull wire can be pulled proximally, thereby releasing the detachment feature from the delivery tube.

The method can further include traversing the implant delivery system through tortuous vasculature. The method can further include inhibiting longitudinal movement of the distal end of the pull wire in relation to the detachment feature by a sleeve providing friction force against the pull wire.

The method can further include aligning the distal end of the pull wire to the distal extension of the detachment feature by a sleeve positioned on the detachment feature and through which the pull wire extends.

Pulling the pull wire proximally, thereby releasing the detachment feature from the delivery tube can further include pulling the pull wire proximally to exit a loop of a loop wire affixed the delivery tube, thereby causing the loop wire to exit an opening through the detachment feature to disengage the detachment feature from the delivery tube.

BRIEF DESCRIPTION OF THE DRAWINGS

The above and further aspects of this invention are further discussed with reference to the following description in conjunction with the accompanying drawings, in which like numerals indicate like structural elements and features in various figures. The drawings are not necessarily to scale, emphasis instead being placed upon illustrating principles of the invention. The figures depict one or more implementations of the inventive devices, by way of example only, not by way of limitation.

DETAILED DESCRIPTION

As used herein, the terms "about" or "approximately" for any numerical values or ranges indicate a suitable dimensional tolerance that allows the part or collection of components to function for its intended purpose as described herein. More specifically, "about" or "approximately" may refer to the range of values ±20% of the recited value, e.g. "about 90%" may refer to the range of values from 71% to 99%.

When used herein, the terms "tubular" and "tube" are to be construed broadly and are not limited to a structure that is a right cylinder or strictly circumferential in cross-section or of a uniform cross-section throughout its length. For example, the tubular structure or system is generally illustrated as a substantially right cylindrical structure. However, the tubular system may have a tapered or curved outer surface without departing from the scope of the present invention.

Systems, implants, and methods are disclosed herein which may be able to attain more precise and repeatable implant detachment. Placement of embolic coils and other implants facing challenges such as partially implanted implants becoming difficult to reposition, shifted delivery systems due to push back during implantation, and/or prematurely released implants may be facilitated. To meet some or all of these needs, example implants can include a detachment feature having a proximal sleeve through which a pull wire can be extended and/or a distal extension which can engage a distal end of the pull wire. The proximal sleeve can be sized, positioned, and otherwise configured to align the pull wire to the distal extension and/or the proximal sleeve can provide a friction force against the pull wire. Preferably, the proximal sleeve provides friction from a disk or tabs that are positioned to press into the pull wire. The disk or tabs can include a biocompatible material(s) that is preferably elastic. The distal extension can provide a hard stop to prevent the distal end of the pull wire from moving further into the implant. The distal extension preferably is shaped in a half-sphere or cone. The sleeve and the distal extension can be respectively formed by milling of the material of the detachment feature and/or attaching material to the detachment feature. Preferably the detachment features can be laser cut from a flat sheet material. The flat sheet material is preferably a radiopaque material that can be welded or otherwise affixed by any suitable means to the embolic coil, braided tube, or other embolic structure of the implant.

Figure 1:
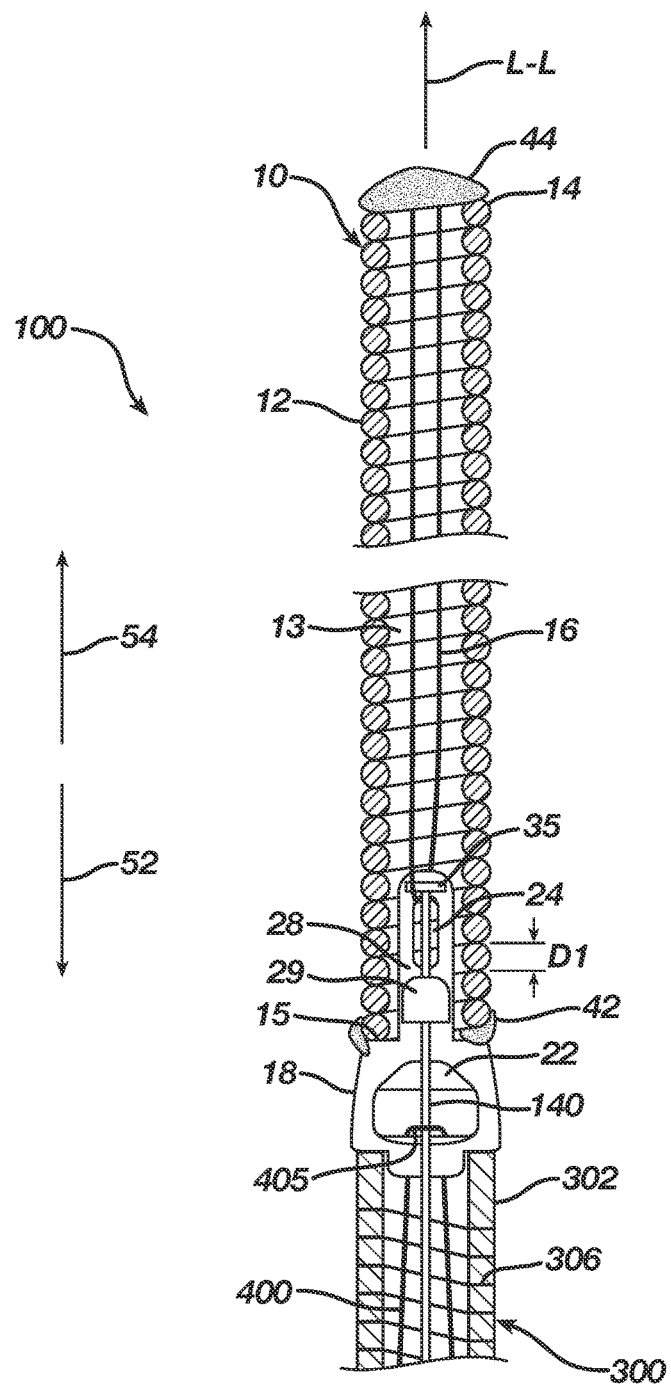
FIG. 1 is an illustration of a cut-away view of an implant attached to a delivery member according to aspects of the present invention.

FIG. 1 is an illustration of a cut-away view an implant 10 attached to a delivery member 300. The implant 10 includes an embolic coil 12, a detachment feature 18, and a stretch resistant fiber 16. Proximal welds 42 join a proximal end 15 of the embolic coil 12 to the detachment feature 18. A distal weld 44 joins a distal end 14 of the embolic coil 12 to the stretch resistant fiber 16. Portions of the coil 12, welds 42, 44, and delivery tube 302 are shown in a cut-away view for the purposes of illustration.

The detachment feature 18 can include a distal opening 24 through which the stretch resistant wire 16 is looped, a proximal opening 22 through which a loop wire 400 extends, a sleeve 29 through which a pull wire 140 extends, and a distal extension 35 positioned to engage a distal end of the pull wire 140. The detachment feature 18 can include a bridge 28 positioned between the distal opening 24 and the proximal opening 22 upon which the sleeve 29 is mounted. The pull wire 140 can extend through a loop opening 405 of the loop wire 400 to secure the detachment feature 18 to the delivery member 300. The loop wire 400 can extend through a lumen of a delivery tube 302 of the delivery member 300 and be under tension, thereby compressing a distal section of the delivery tube 302 having a spiral cut 306.

Example delivery members and engagement/deployment systems are described in U.S. Pat. Nos. 10,806,461 and 10,806,462 each incorporated herein by reference.

Figure 2:
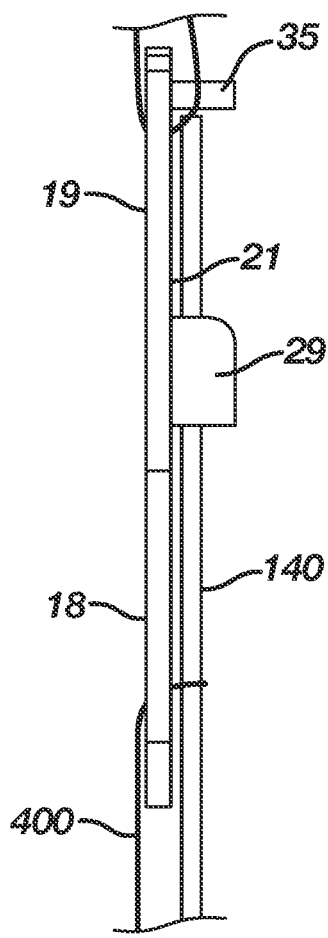
FIG. 2 is an illustration of a side view of a detachment feature according to aspects of the present invention.

FIG. 2 is an illustration of a side view of the detachment feature 18, loop wire 400, and pull wire 140. The embolic coil 12 and the delivery tube 302 are omitted for the sake of the illustration. The detachment feature 18 can have a substantially flat profile, which provides flexibility in directions into and out of the page in relation to the orientation illustrated in FIG. 1. The detachment feature 18 can have a planar back side 19 and a front side 21 opposite the planar back side 19. The distal extension 35 and the sleeve 29 are positioned on the front side 21.

The distal extension 35, sleeve 29, and/or bridge 28 can each facilitate in reducing instances of premature deployment. The detachment feature 18 can include any combination of these features.

The bridge 28 can be positioned distally from the proximal opening 22. As the loop wire 400 presses into the pull wire 140 at the proximal opening 22 of the detachment feature 18, the pull wire 140 may bend in response. The bridge 28 can provide an opposite force to support the pull wire 140 and provide a limit to which the pull wire 140 is able to bend.

The sleeve 29 can provide a friction force against the pull wire 140 to inhibit longitudinal movement of the pull wire 140. The sleeve is preferably positioned on the bridge 28; however, the sleeve can alternatively be positioned in a proximal direction 52 in relation to the proximal opening 22 or in a distal direction 54 in relation to the distal opening 24. When the detachment feature 18 includes the distal extension 35 and the sleeve 29, the sleeve can function to align the pull wire 140 to the distal extension 35, in which case the sleeve 29 may or may not also provide a friction force against the pull wire 140 to inhibit longitudinal movement of the pull wire 140.

The distal extension 35 is preferably at a distal end of the detachment feature 18 so that the pull wire 140 can have maximum extension through the loop opening 405 of the loop wire 400 without reducing flexibility of the embolic coil 12.

To facilitate repositioning of the implant, the stretch resistant fiber 16 can extend through the embolic coil 12 and limit separation of windings of the coil 12 when the coil 12 is bent and/or pulled. By limiting the separation of the windings, the embolic coil 12 is less likely to become tangled when partially implanted and less likely to be stretched or otherwise deformed when retracted. The embolic coil 12 can thereby be more easily repositioned compared to an embolic coil lacking the stretch resistant fiber 16.

To reduce effects of push back during implantation, the detachment feature 18 can be sized and affixed to the embolic coil 12 to provide an embolic coil implant 10 with a highly flexible proximal section. An embolic coil implant 10 having a highly flexible proximal section can reduce push back force on the delivery tube 302 and thereby mitigate the effects of the delivery tube 302 shifting. Additionally, or alternatively, the detachment feature 18 can be sized to mate with a delivery tube 302 having a highly flexible distal section, and the highly flexible distal section of the delivery tube can mitigate the effects of the delivery tube shifting. When an embolic coil implant 10 having a highly flexible proximal section is mated to a delivery tube 302 having a highly flexible distal portion, the combination of the flexible distal section of the delivery tube 302 and the flexible proximal section of the implant 10 can further mitigate the effects of delivery tube shifting. Although not illustrated, the detachment feature 18 can be tapered as it extends further within a lumen 13 of the embolic coil 12 to allow the embolic coil 12 to have additional flexibility where the embolic coil 12 surrounds the tapered region. The flat profile of the detachment feature 18 and the minimal number of fused windings near the proximal end 15 of the coil 18 can also allow for high flexibility near the proximal end 15 of the embolic coil 12.

Figure 3A:
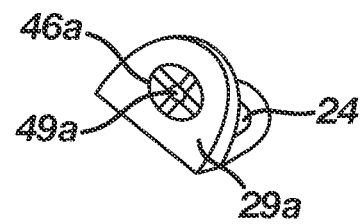
FIGS. 3A through 3C are illustrations of a sleeve of the detachment feature according to aspects of the present invention.
Figure 3B:
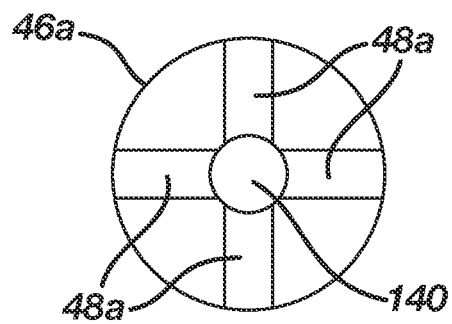
Figure 3C:
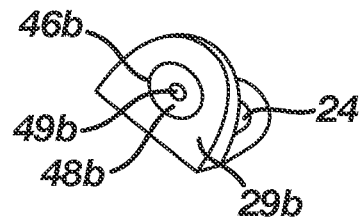

FIGS. 3A through 3C are illustrations of the sleeve 29 of the detachment feature 18. FIG. 3A is a perspective view of a first example sleeve 29a and the distal opening 24 of the detachment feature 18. FIG. 3B is a planar view of a sleeve opening 46a of the first example sleeve 29a. The first example sleeve 29a includes tabs 48a extending inwardly from a perimeter of the sleeve opening 46a to converge on a pull wire opening 49a. FIG. 3C is a perspective view of a second example sleeve 29b and the distal opening 24 of the detachment feature 18. The second example sleeve 29b includes a disk 48b within a sleeve opening 46b. The disk 48b has a pull wire opening 49b at its center.

The tabs 48a and disk 48b of the sleeve 29a, 29b can include a biocompatible material that is preferably elastic. The tabs 48a and disk 48b of the sleeve 29a, 29b can include one or more bioabsorbable materials. Example suitable materials can include silicone, alumina, bioglass, stainless steel, cobalt-chromium alloy, ceramic biomaterial (e.g., hydroxyapatite or zirconia), and polymers (e.g., polyvinylchloride (PVC), polyethylene (PE), polypropylene (PP), polytetrafluoroethylene (PTFE), polymethylmethacrylate (PMMA), trimethylcarbonate, TMC NAD-lactide, polycaprolactone (PCA), polylactic acid (PLA), polycaprolactone (PCL), polyglycolic acid (PGA), polydioxanone (PDO), polybutyrolactone (PBL), polyvalerolactone (PVL), and poly(lactide-co-glycolide) (PLGA)).

Figure 4A:
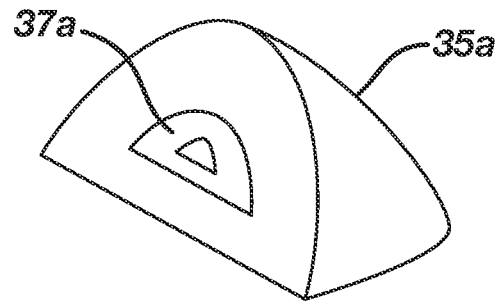
FIGS. 4A and 4B are illustrations of a distal extension of the detachment feature according to aspects of the present invention.
Figure 4B:
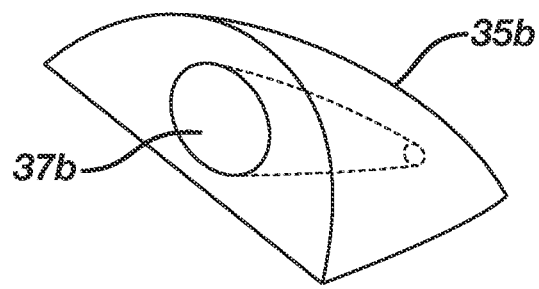

FIGS. 4A and 4B are illustrations of the distal extension 35 of the detachment feature 18. FIG. 4A illustrates a first example distal extension 35a having a shallow cavity 37a for receiving the distal end of the pull wire 140. FIG. 4B illustrates a second example distal extension 35b having a deeper cavity 37b for receiving the distal end of the pull wire 140. Preferably the distal extension 35 has a semi-conical shape such as illustrated in FIGS. 4A and 4B.

Figure 5:
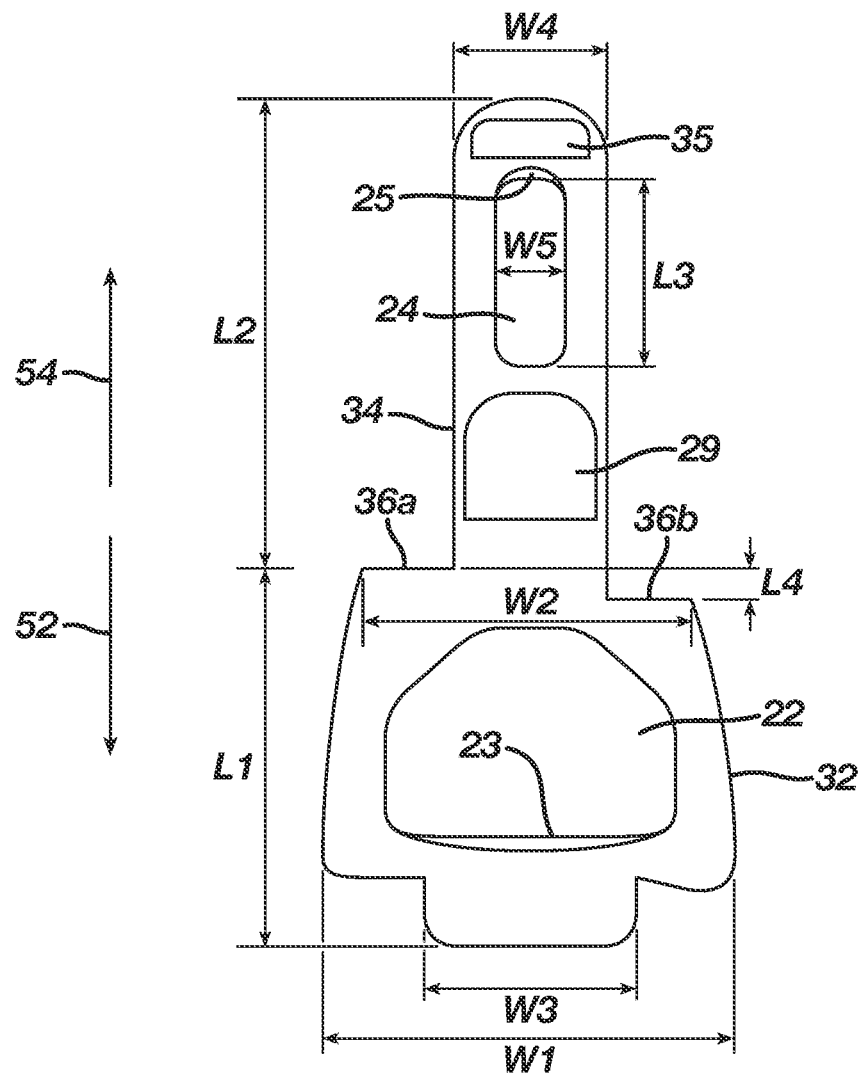
FIG. 5 is an illustration of dimensions of the detachment feature of the implant according to aspects of the present invention.

FIG. 5 is an illustration of dimensions of the detachment feature 18. The proximal portion 32 has a first length L1 measured from a proximal end of the detachment feature 18 to a shoulder 36a of the detachment feature 18. The distal portion 34 has a second length L2 measured from the shoulder 36a to a distal end of the detachment feature 18. The distal opening 24 of the detachment feature 18 has a third length L3. The detachment feature 18 can have a first shoulder 36a and a second shoulder 36b opposite the first shoulder 36a. The shoulders 36a, 36b can be configured to be welded or otherwise affixed to the proximal end 15 of the embolic coil 12. The shoulders 36a, 36b can be offset by a fourth length L4. The fourth length L4 can be dependent upon a thickness of windings of the coil 12. Preferably, the fourth length L4 measures about half of a diameter D1 a winding of the coil 12 (see FIG. 1).

The proximal portion 32 has a first width W1 that is a maximum width of the proximal portion 32, a second width W2 that is a minimum width of a main part of the proximal portion 32, and a third width W3 of a proximal extension 38. The proximal extension 38 is sized to fit within a lumen of the delivery tube 302, therefore the third width W3 is less than, and preferably approximately equal to, a diameter of the lumen of the delivery tube 302. The distal portion 34 of the detachment feature 18 has a fourth width W4 that is less than a diameter of the lumen 13 of the embolic coil 12. In some examples, although not illustrated, the width of the distal portion can taper, becoming narrower in the distal direction 54 of the detachment feature 18 to improve flexibility of the embolic coil 12 near the proximal end 15 of the coil. The distal opening 24 of the detachment feature 18 can have a fifth width W5.

The proximal opening 22 can have an atraumatic surface 23 against which the loop wire 400 can press to minimize abrasion to the loop wire 400 by the detachment feature 18. The distal opening 24 can have an atraumatic surface 25 against which the stretch resistant fiber 16 can press to minimize abrasion to the stretch resistant fiber 16 by the detachment feature 18.

Figure 6:
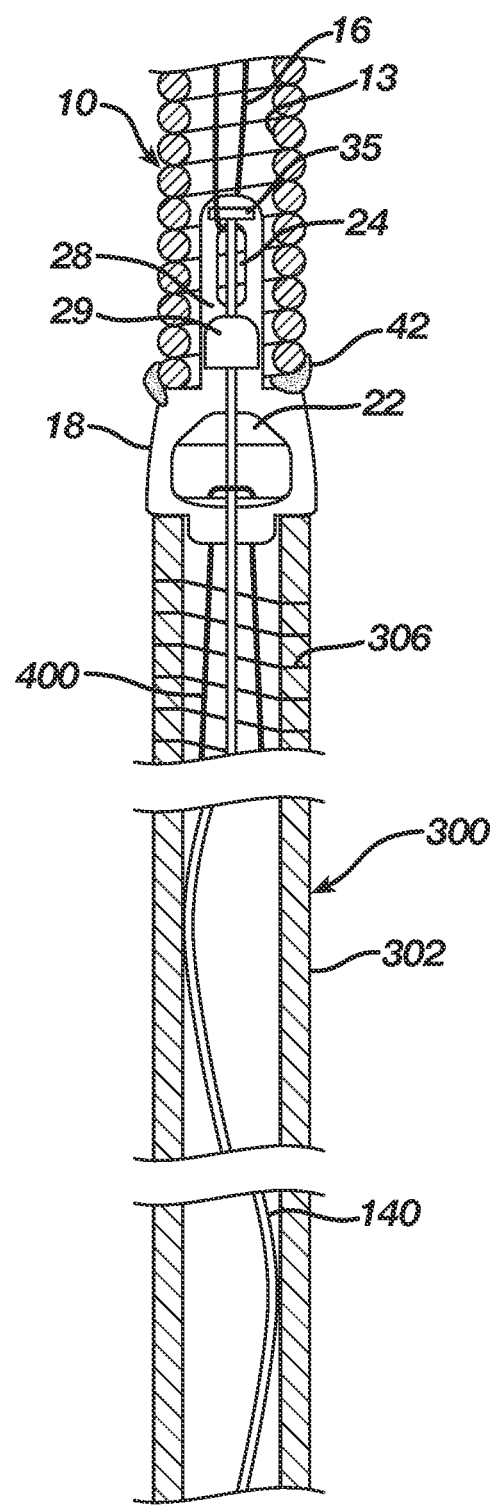
FIG. 6 is an illustration of a cut-away view of the implant attached to the delivery member with a pull wire under compression according to aspects of the present invention.

FIG. 6 is an illustration of a cut-away view of the implant 10 attached to the delivery member 300 with the pull wire 140 under compression. Because the distal extension 35 inhibits the pull wire 140 from moving distally into the embolic coil 12, the pull wire 140 can be loaded under compression within the delivery tube 302.

Figure 7:
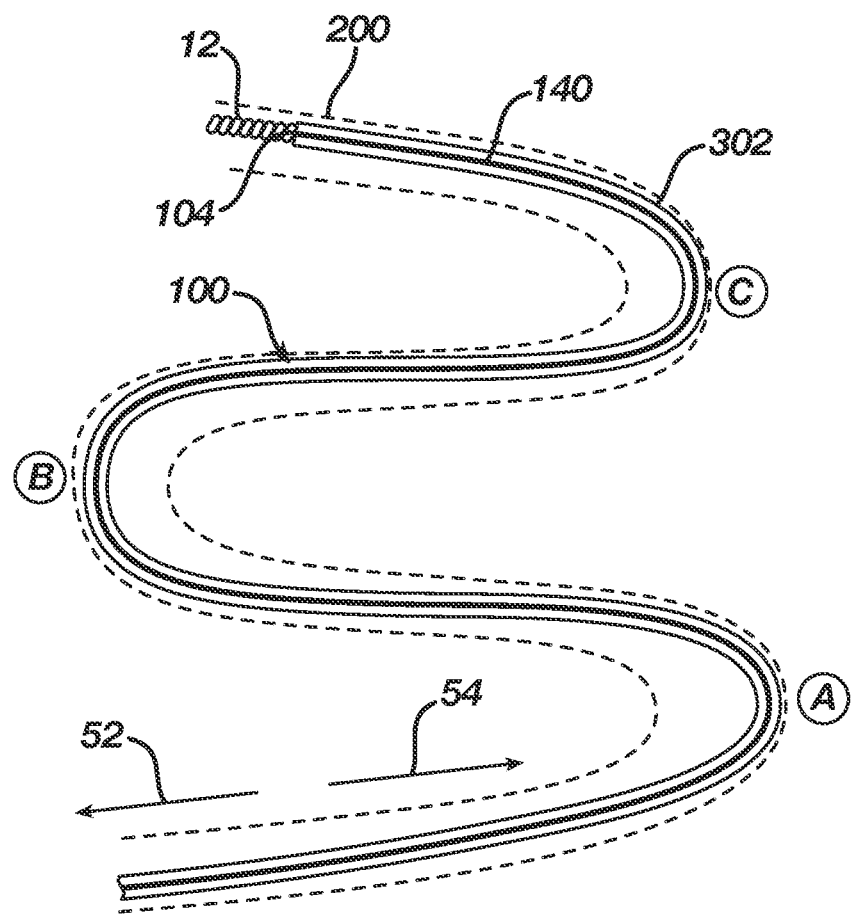
FIG. 7 is an illustration of a system including the implant and delivery member navigating vasculature according to aspects of the present invention.

FIG. 7 is an illustration of a system 100 including the implant 10 and delivery member 300 navigating vasculature through a guide catheter 200. As the system 100 navigates bends A, B, C the system 100 tends to extend to the extremes of the bends A, B, C. Similarly, as the delivery tube 302 bends, the pull wire 140 tends to move to extremes of the delivery tube 302 at the bends A, B, C. Without placing the pull wire 140 under compression as illustration in FIG. 6 and without providing a friction force from the sleeve 29 to the pull wire 140, the distal end of the pull wire 140 can move in the proximal direction 52 in relation to the loop wire opening 405 as the system 100 navigates the bends A, B, C. In extreme circumstances, the distal end of the pull wire 140 can travel proximally past the loop wire opening 405 to cause premature release of the implant 10.

As described here, however, by placing the pull wire 140 under compression as illustrated in FIG. 6, the pull wire 140 has slack to accommodate movement to the extremes of the delivery tube 302 in the bends. If the detachment feature 18 includes a sleeve 29 that provides frictional force against the pull wire 140, the sleeve can provide tension to the pull wire 140 to prevent the pull wire 140 from moving to the extremes of the delivery tube 302. These mitigating measures can be used alone or in combination to reduce the likelihood of premature release of the implant 10.

FIGS. 8A through 8D are a sequence of illustrations depicting detachment of the implant 10 from the delivery member 300. A portion of the delivery tube 302 and a portion of the embolic coil 12 are cut away for illustration purposes.

Figure 8A:
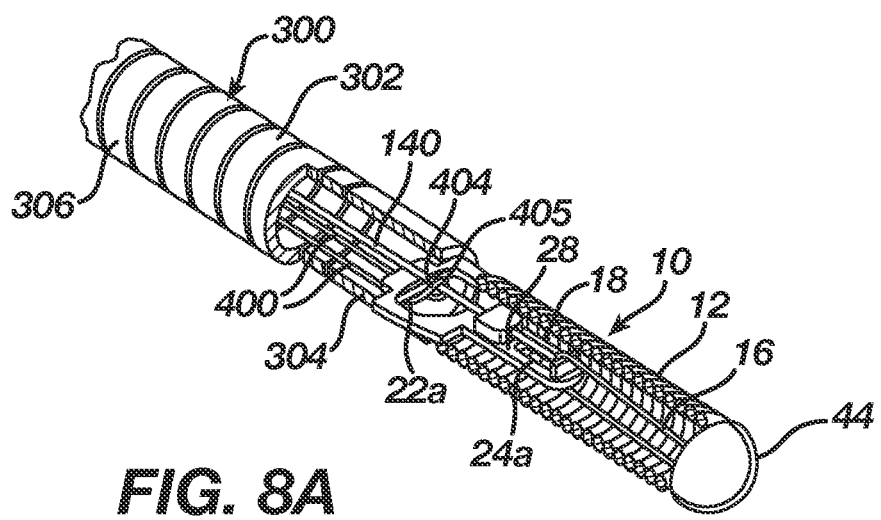
FIG. 8A through 8D are a sequence of illustrations depicting detachment of the implant from the delivery member according to aspects of the present invention.

FIG. 8A illustrates the engagement system including the pull wire 140 and the loop wire 400 in a locked configuration on the detachment feature 18 of the implant 10. The delivery tube 300 includes a compressible portion 306 that can be compressed. The detachment feature 18 is secured to the delivery tube 302 by the loop wire 400 and the pull wire 140 as described in greater detail in relation to FIG. 1.

Figure 8B:
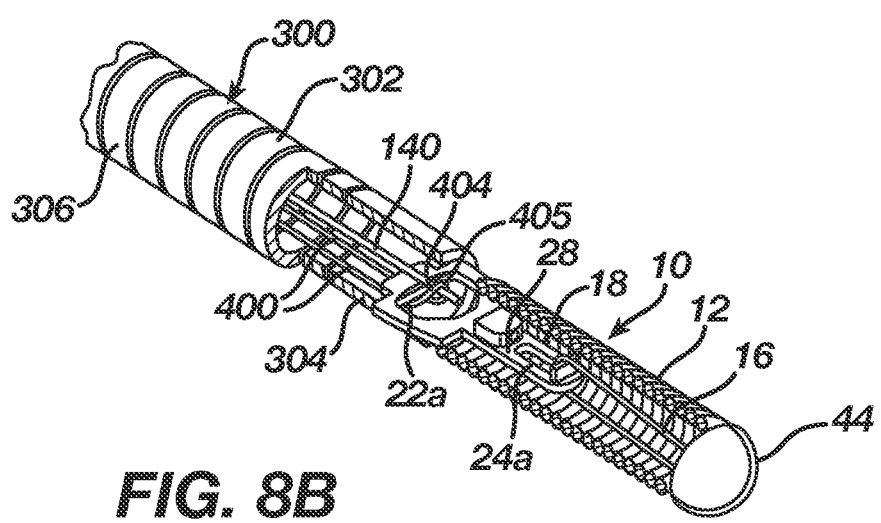

FIG. 8B illustrates the pull wire 140 being drawn proximally to begin the release sequence for the implant 10. The pull wire 140 proximally exits the distal extension 35 and/or the sleeve 29 of the detachment feature 18.

Figure 8C:
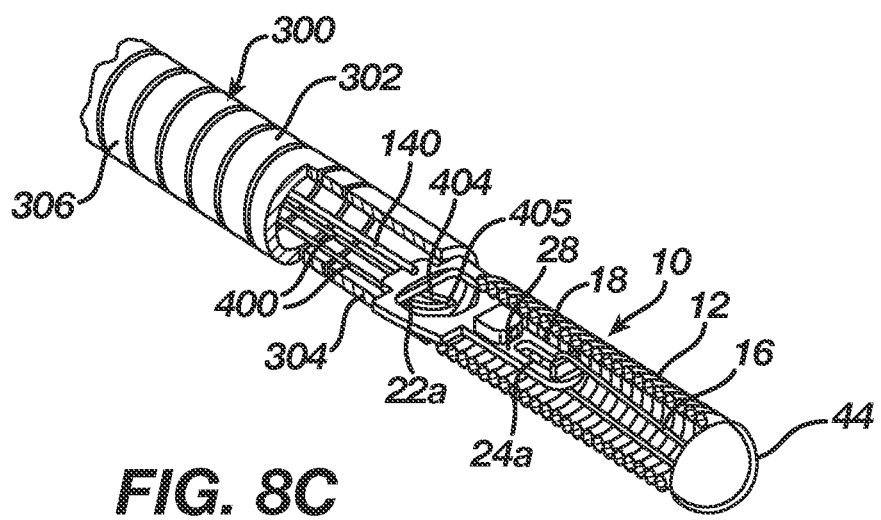

FIG. 8C illustrates the instant the pull wire 140 exits the opening 405 of the loop wire 400, allowing the distal end 404 of the loop wire 400 to fall away and exit the detachment feature 18. As shown, there is now nothing holding the implant 10 to the delivery tube 300.

Figure 8D:
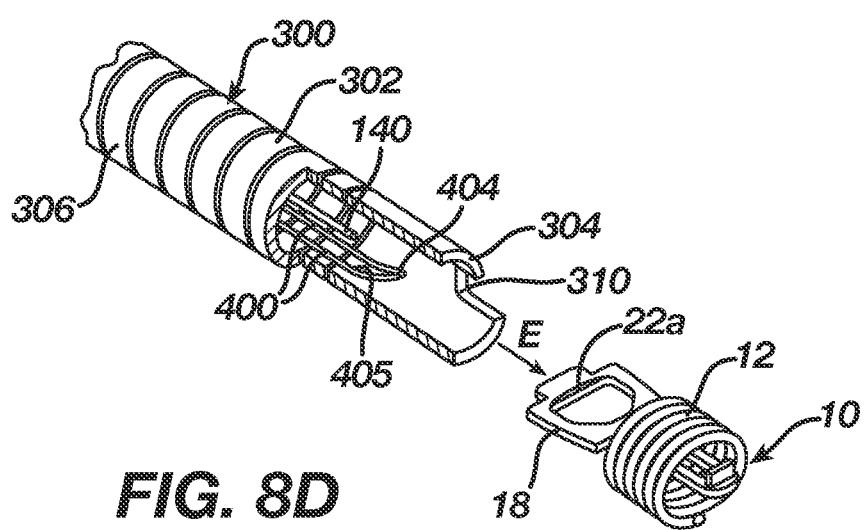

FIG. 8D illustrates the end of the release sequence. Here, the compressible portion 306 has expanded/returned to its original shape and "sprung" forward. An elastic force E is imparted by the distal end 304 of the delivery tube 300 to the implant 10 to "push" it away to ensure a clean separation and delivery of the implant 10. As made visible in FIG. 8D, the delivery tube 302 can include a notch 310 sized and configured to receive the proximal portion 32 of the detachment feature 18 of the implant 10, and likewise the proximal portion 32 of the detachment feature 18 can be sized to fit within the notch 310 of the delivery tube 302.

Figure 9A:
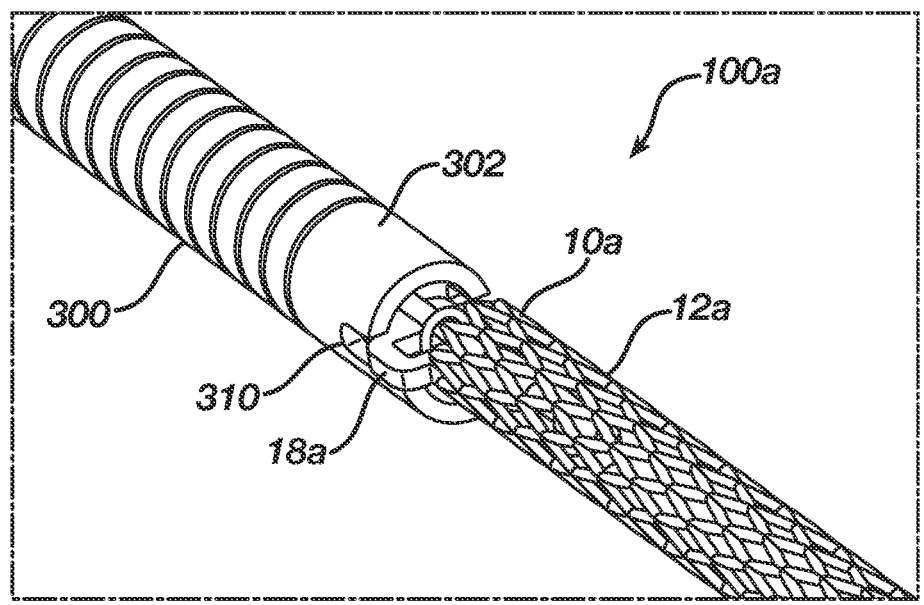
FIGS. 9A through 9B are illustrations of an alternative implant attached to the delivery system according to aspects of the present invention.
Figure 9B:
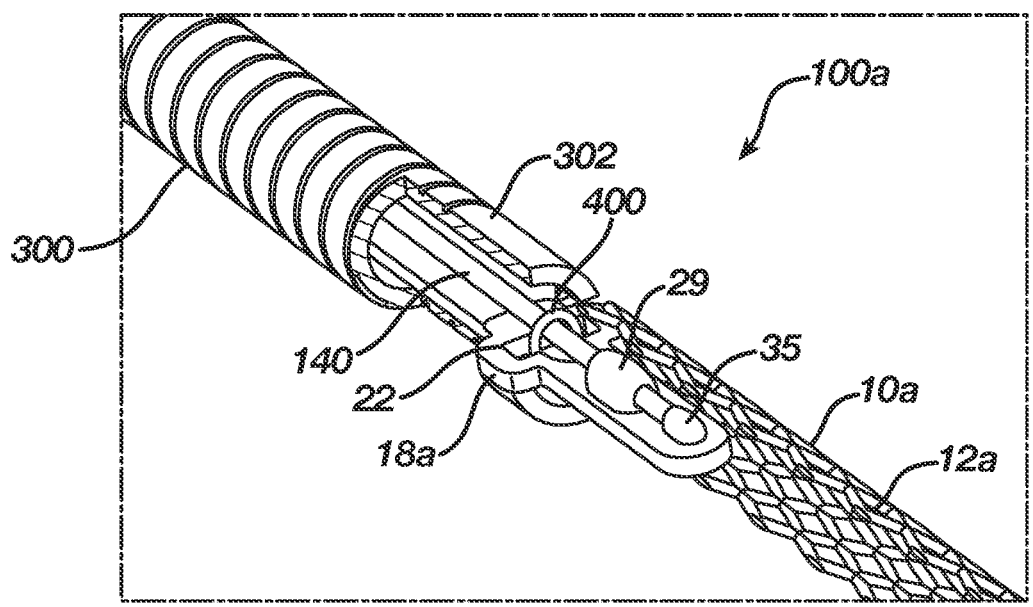

FIGS. 9A through 9B are illustrations of an alternative system 100a including an alternative implant 10a attached to the delivery member 300. The implant 10a includes a tubular braid 12a in place of the embolic coil 12. The detachment feature 18a lacks the distal opening 24 and is otherwise similarly configured to the detachment feature 18 described and illustrated elsewhere herein. The system 100a is configured to deliver the implant 10a as illustrated in both FIGS. 9A and 9B. A portion of the delivery tube 302 and a portion of the braid 12a are cut away in FIG. 9B for the sake of illustration.

Figure 10:
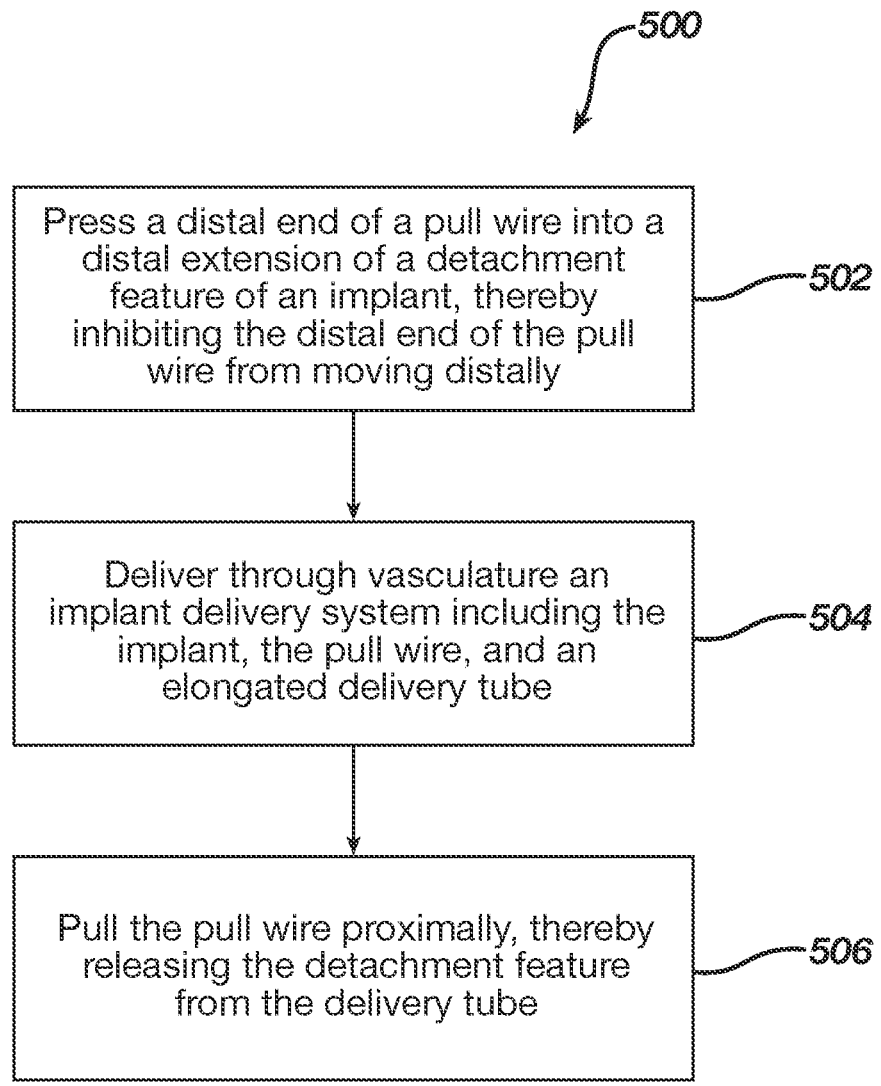
FIG. 10 is a flow diagram of a method of delivering and releasing an example implant according to aspects of the present invention.

FIG. 10 is a flow diagram of a method 500 of delivering and releasing an example implant. The method 500 can be applied to any of the example implants 10, 10a disclosed herein, variations thereof, and alternatives thereto as understood by a person skilled in the pertinent art.

At step 502, a distal end of a pull wire can be pressed into a distal extension of a detachment feature of an implant, thereby inhibiting the distal end of the pull wire from moving distally. The pull wire, detachment feature, and distal extension can respectively be configured similarly to corresponding components 140, 18, 35 disclosed herein, variations thereof, and alternatives thereto as understood by a person skilled in the pertinent art.

At step 504, an implant delivery system, including the implant, the pull wire, and an elongated delivery tube, can be delivered through vasculature. The implant delivery system can be configured similarly to the implant delivery systems 100, 100a disclosed herein, variations thereof, and alternatives thereto as understood by a person skilled in the pertinent art. The elongated delivery tube can be configured similarly to the delivery tube 300 disclosed herein, variations thereof, and alternatives thereto as understood by a person skilled in the pertinent art. The vasculature through which the delivery system is delivered can be tortuous. As the delivery system is delivered through tortuous vasculature, longitudinal movement of the distal end of the pull wire can be inhibited by a sleeve providing friction force against the pull wire. The sleeve can be configured similarly to the example sleeve 29 disclosed herein, variations thereof, and alternatives thereto as understood by a person skilled in the pertinent art. The distal end of the pull wire can be aligned to the distal extension by the sleeve.

At step 506, the pull wire can be pulled proximally to release the detachment feature from the delivery tube. The pull wire can be pulled proximally through a loop of a loop wire affixed to the delivery tube, thereby causing the loop wire to exit an opening of the detachment feature to disengage the detachment feature from the delivery tube.

The descriptions contained herein are examples of embodiments of the invention and are not intended in any way to limit the scope of the invention. As described herein, the invention contemplates many variations and modifications of the implant and methods for making and using the same, including alternative materials (including bioabsorbable materials), alternative geometries of component parts, alternative positioning of component parts in relation to each other, etc. Modifications apparent to those skilled in the pertinent art to which this invention relates and are intended to be within the scope of the claims which follow.

What is claimed is:

1. A system comprising:
    an elongated delivery tube configured to traverse vasculature and extending along a longitudinal axis of the system;
    an embolic implant comprising a detachment feature, the detachment feature comprising a distal extension and a proximal opening;
    a loop wire affixed to the delivery tube and extending through the proximal opening of the detachment feature; and
    a pull wire extending through the delivery tube, extending through an opening in the loop wire, and inhibited from moving distally by the distal extension of the detachment feature,
    wherein the embolic implant further comprises:
    an embolic coil; and
    a stretch resistant fiber;
    wherein a distal portion of the detachment feature is positioned within a lumen of the embolic coil,
    wherein the distal portion comprises the distal extension,
    wherein a proximal portion of the detachment feature extends proximally from a proximal end of the embolic coil,
    wherein the proximal portion comprises the proximal opening,
    wherein the distal portion of the detachment feature further comprises a distal opening,
    and wherein the stretch resistant fiber passes through the distal opening and extends through the lumen of the embolic coil to a distal end of the embolic coil, the stretch resistant fiber being effective to limit separation of windings of the embolic coil as the embolic coil is under tension.

2. The system of claim 1,
    wherein the detachment feature further comprises a sleeve into which the pull wire extends, and
    wherein the sleeve provides a friction force against the pull wire.

3. The system of claim 2,
    wherein the sleeve comprises an elastic material positioned on at least a portion of a perimeter of an opening of the sleeve and providing the friction force against the pull wire, and
    wherein the pull wire extends through the opening of the sleeve.

4. The system of claim 1,
    wherein the detachment feature further comprises a sleeve through which the pull wire extends, and
    wherein the sleeve is positioned to align the pull wire longitudinally with the distal extension.

5. The system of claim 1, wherein the proximal portion comprises a proximal width that is greater than a distal width of the distal portion.

6. The system of claim 1,
    wherein the detachment feature comprises a first shoulder affixed to the proximal end of the embolic coil and a second shoulder affixed to the proximal end of the embolic coil, and
    wherein the first shoulder is longitudinally offset in relation to the second shoulder.

7. The system of claim 1,
    wherein the elongated delivery tube comprises notches extending proximally from a distal end of the delivery tube, and
    wherein a proximal portion of the detachment feature is positioned within the notches.

8. The system of claim 1, wherein the proximal opening comprises an atraumatic surface against the loop wire.

9. The system of claim 1,
    wherein the detachment feature comprises a substantially planar first surface and a second surface opposite the first surface, and
    wherein the distal extension is disposed on the second surface.

10. The system of claim 1,
    wherein the pull wire is in compression longitudinally within the delivery tube.

11. A system comprising:
    an embolic tube comprising a lumen therethrough and defining a longitudinal axis;
    a detachment feature comprising:
        a distal portion extending within the lumen,
        a proximal portion extending proximally from a proximal end of the embolic tube,
        a proximal opening configured to receive a loop wire therethrough, and
        a sleeve comprising a longitudinal opening configured to receive a pull wire;
    a loop wire affixed to an extended delivery tube and extending through the proximal opening of the detachment feature;
    a pull wire extending through the delivery tube, extending through an opening in the loop wire, and inhibited from moving distally by the distal portion of the detachment feature; and
    a stretch resistant fiber
    wherein the proximal portion comprises the proximal opening,
    wherein the distal portion of the detachment feature further comprises a distal opening, and
    wherein the stretch resistant fiber passes through the distal opening and extends through the lumen of the embolic tube to a distal end of the embolic tube, the stretch resistant fiber being effective to limit separation of windings of the embolic tube as the embolic tube is under tension.

12. The system of claim 11, wherein the detachment feature further comprises a distal extension positioned distally of the sleeve and aligned longitudinally with the longitudinal opening.

13. The system of claim 11, wherein the sleeve comprises an elastic material on at least a portion of a perimeter of the longitudinal opening.

14. A method of delivering an implant comprising a detachment feature, the method comprising:
- inhibiting a distal end of a pull wire from moving distally by pressing the distal end of the pull wire into a distal extension of the detachment feature;
- delivering an implant delivery system through vasculature, the implant delivery system comprising an elongated delivery tube, the implant, and the pull wire; and
- pulling the pull wire proximally, thereby releasing the detachment feature from the delivery tube,
- wherein pulling the pull wire proximally, thereby releasing the detachment feature from the delivery tube further comprises pulling the pull wire proximally to exit a loop of a loop wire affixed to the delivery tube, thereby causing the loop wire to exit an opening through the detachment feature to disengage the detachment feature from the delivery tube.

15. The method of claim 14, further comprising:
- traversing the implant delivery system through tortuous vasculature; and
- inhibiting longitudinal movement of the distal end of the pull wire in relation to the detachment feature by a sleeve providing friction force against the pull wire.

16. The method of claim 14, further comprising:
- aligning the distal end of the pull wire to the distal extension of the detachment feature by a sleeve positioned on the detachment feature and through which the pull wire extends.

* * * * *